United States Patent
Kramer et al.

(10) Patent No.: US 6,531,512 B1
(45) Date of Patent: Mar. 11, 2003

(54) METHOD OF TREATING CANCER IN PATIENTS HAVING A DEFICIENCY IN P53 TUMOR SUPPRESSOR GENE

(75) Inventors: Debora L. Kramer, East Aurora, NY (US); Carl W. Porter, East Aurora, NY (US)

(73) Assignee: Health Research Inc., Buffalo, NY (US)

( * ) Notice: Subject to any disclaimer, the term of this patent is extended or adjusted under 35 U.S.C. 154(b) by 0 days.

(21) Appl. No.: 09/743,120

(22) PCT Filed: Jul. 29, 1999

(86) PCT No.: PCT/US99/17193

§ 371 (c)(1), (2), (4) Date: Mar. 12, 2001

(87) PCT Pub. No.: WO00/06136

PCT Pub. Date: Feb. 10, 2000

Related U.S. Application Data

(60) Provisional application No. 60/094,795, filed on Jul. 31, 1998.

(51) Int. Cl.⁷ ............................................... A61K 31/13
(52) U.S. Cl. .................. 514/674; 514/642; 514/647; 514/922; 436/501; 436/503; 436/504; 436/512; 436/516; 436/64
(58) Field of Search ................. 514/642, 647, 514/674, 922; 436/501, 503, 504, 64, 512, 516

(56) References Cited

U.S. PATENT DOCUMENTS 5,382,510 A * 1/1995 Levine et al. .................. 435/6
5,456,908 A 10/1995 Aziz et al.
5,541,230 A 7/1996 Basu et al.
5,723,302 A 3/1998 Diamandis
5,880,161 A 3/1999 Basu et al.

FOREIGN PATENT DOCUMENTS

WO  WO 88/00947  2/1988

OTHER PUBLICATIONS

Gosland et al., "Reversal of doxurubicin, etoposide, vinblastine, and taxol resistance in multidrug resistant human sarcoma cells by a polymer of spermine", Cancer Chemother. Pharmacol. Feb. 24, 1995, pp. 593–600.

Basu et al., "The ability of Polyamine Analogues to Induce Z–DNA Structure in Synthetic . . . ", Anticancer Research, 1996, pp. 39–48.

Marverti et al., "$N^1$, $N^{12}$–bis(ethyl)spermine effect of growth of cis–diamminedichloroplatinum(II)–sensitive . . . ", Int. J. Cancer, 1998, pp. 33–40.

Hawthorne et al., "Synergism of the polyamine analogue, $N^1$, $N^{11}$–bisethylnorspermine with cis–diaminedichloroplatinum(II) against murine neoplastic cell lines in vitro and in vitro", Cancer Letters, 1996, pp. 99–107.

Kramer et al., Polyamine Analogue Induction of the p53–p21 $^{WAF1/CIP1}$–Rb Pathway and $G_1$ Arrest in Human Melanoma Cells, Cancer Research, 1999, pp. 1278–1286.

* cited by examiner

Primary Examiner—Frederick Krass
(74) Attorney, Agent, or Firm—Merchant & Gould P.C.

(57) ABSTRACT

A method of treating cancer in a patient deficient in p53 tumor suppression gene is described herein by administering to a patient a therapeutically effective amount if a polyamine such as DENSPM in combination with an anticancer agent. Also described is a method of selecting patients for cancer treatment with a polyamine, for example, DENSPM.

16 Claims, 7 Drawing Sheets

US 6,531,512 B1

METHOD OF TREATING CANCER IN PATIENTS HAVING A DEFICIENCY IN P53 TUMOR SUPPRESSOR GENE

This application is a 371 of PCT/US99/17193, filed Jul. 29, 1999, which claims the benefit of U.S. Provisional Application No. 60/094,795, filed Jul. 31, 1998.

FIELD OF THE INVENTION

This invention concerns a method for treating cancer in patients having deficiency in p53 tumor suppressor gene.

BACKGROUND OF THE INVENTION

Progression through the cell cycle is controlled by the combined effects of kinases, phosphatases and inhibitory proteins mediated by protein partnering and positive- and negative-acting phosphorylation. The cyclin D1-cdk4-pRb pathway is activated in $G_1$ and initiates progression towards S-phase (DelSal et al. (1996) *Critical Rev. in Oncogen.* 7:127–142).

Cell cycle progression is characterized by checkpoints where the cell determines whether previous steps have been successfully completed before moving forward. The p53 network serves as a molecular sensor for the $G_1$ checkpoint and monitors DNA damage, nucleotide pool levels, mitotic spindle status and genotoxic stress (Luo et al. (1995) *Nature* 375:159–161; and Agarwal et al. (1998) *J. Biol. Chem.* 273:1–4). Additionally, the p53 network regulates cell cycle progression, programmed cell death, replicative senescense and possibly differentiation. In the DNA damage pathway (Kastan et al. (1991) *Cancer Res.* 51:6304–6311), p53 increases in amount via protein stabilization and transcriptionally activates several genes. Among other events, induction of p53 leads to transcriptional activation of the cyclin dependent kinase inhibitor, p21, which in turn, causes hypophosphorylation of the retinoblastoma protein (Rb), increased binding of Rb to the transcription factor E2F and reduced expression of S-phase specific genes. In the absence of the latter gene products, a $G_1/S$ cell cycle arrest ensues. Increases in p53 can either promote apoptosis or $G_1$ arrest depending on the genotype of the cell and the nature of the cellular insult.

Loss of wild-type p53 (wt-p53) function generally leads to uncontrolled cell cycling and replication, inefficient DNA repair, selective growth advantage and, hence, tumor formation. In fact, the p53 gene is mutated in more than 50% of tumors (Beroud et al. (1996) *Nucl. Acids Res.* 24:147–150).

SUMMARY OF THE INVENTION

This invention relates to a method for treating cancer in patients having a deficiency in p53 tumor suppressor gene function. More particularly, the invention provides a method for treating cancer, e.g., preferably a solid tumor, which includes administering to a patient suffering therefrom a therapeutically effective amount of a polyamine of the formula:

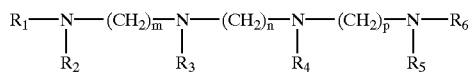

wherein:

$R_1$, $R_2$, $R_3$, $R_4$, $R_5$ and $R_6$ independently are hydrogen or $C_1$–$C_{12}$ alkyl; m, n and p are independently integers from 3 to 6;

or a pharmaceutically acceptable salt thereof, provided at least one of $R_1$, $R_2$, $R_5$ and $R_6$ is $C_1$–$C_{12}$ alkyl, in combination with at least one anticancer agent in unit dosage form.

The method preferably is carried out employing a polyamine of the above formula wherein $R_1$ and $R_6$ both are $C_1$–$C_6$ alkyl, especially ethyl, and $R_2$, $R_3$, $R_4$ and $R_5$ are hydrogen. The method is ideally carried out utilizing a polyamine of the above formula where n, m and p independently are 3 or 4.

A particularly valuable compound employed in the method of the invention is the polyamine where m, n and p are 3. This compound is known as bis-ethylnorspermine or $N^1,N^{11}$-diethylnorspermine (DENSPM).

The method of treating cancer of the present invention involves administering a therapeutically effective amount of a polyamine as above defined in combination with an anticancer agent in unit dosage form. Anticancer agents include, but are not limited to, cisplatin, carboplatin, camptothecins, doxorubicin, cyclophosphamide, or etoposide.

Treatment of the patient may be carried out by administering the polyamine and the anticancer agent concurrently but in separate unit dosage forms, preferably by parenteral administration. Alternatively, the polyamine and the anticancer agents may be administered together in a so-called "cocktail". The method of the present invention for treating cancer preferably is used in treating solid tumors, for example, non-small cell lung carcinoma, prostate carcinoma, renal carcinoma, colon carcinoma, ovarian carcinoma, pancreatic carcinoma, and melanoma.

A second aspect of the invention provides an in-vitro method of selecting patients for cancer treatment with a polyamine as defined above including the steps of isolating tumor cells from the patients; determining whether or not the tumor cells are deficient in p53 tumor suppressor gene function; and treating patients having tumors deficient in p53 tumor suppressor gene with a polyamine as above defined. Additionally, the invention provides a method of treating a tumor in a mammal and a method of inducing tumor cell apoptosis.

DETAILED DESCRIPTION OF THE PREFERRED EMBODIMENT

This invention relates to a method for treating cancer in patients having a deficiency in p53 tumor suppressor.

Tumor Suppressor Gene

The human p53 gene is located in a 16 to 20 kb segment of DNA on the short arm of chromosome 17 at position 17p13.1. The gene has 11 exons and produces a mRNA of 2.2 kb in size that is expressed in all tissues of the body (Levine et al. (1994) *J. Lab. Clin. Med.* 123:817). The nucleotide sequence of the gene and amino acid sequence of the p53 protein has been largely conserved. In fact, amino acid sequence identity approaches 100% in five regions of the protein which encompass amino acid residues 13 to 19 (I), 120 to 143 (II), 172 to 182 (III), 238 to 259 (IV) and 271 to 289 (V), out of a total of 393 amino acid residues (Levine, supra).

As used herein, the term "deficient in p53 tumor suppressor gene" refers to an organism having a p53 tumor suppressor gene that is inactivated, mutated, lost or underproduced. For example, functional inactivation may occur as a consequence of genetic aberrations within the p53 gene or interaction with viral and cellular oncogenes. Examples of mutations include missense mutations producing faulty or altered proteins, deletions or insertions (in or out of the reading frame), nonsense mutations (chain termination), frameshift mutations. Frequently the mutations are missense mutations localized in the highly conserved regions, most typically regions II, III, IV and V of the protein (Levine, supra).

p53/p21/Rb Pathway

Figure 7:
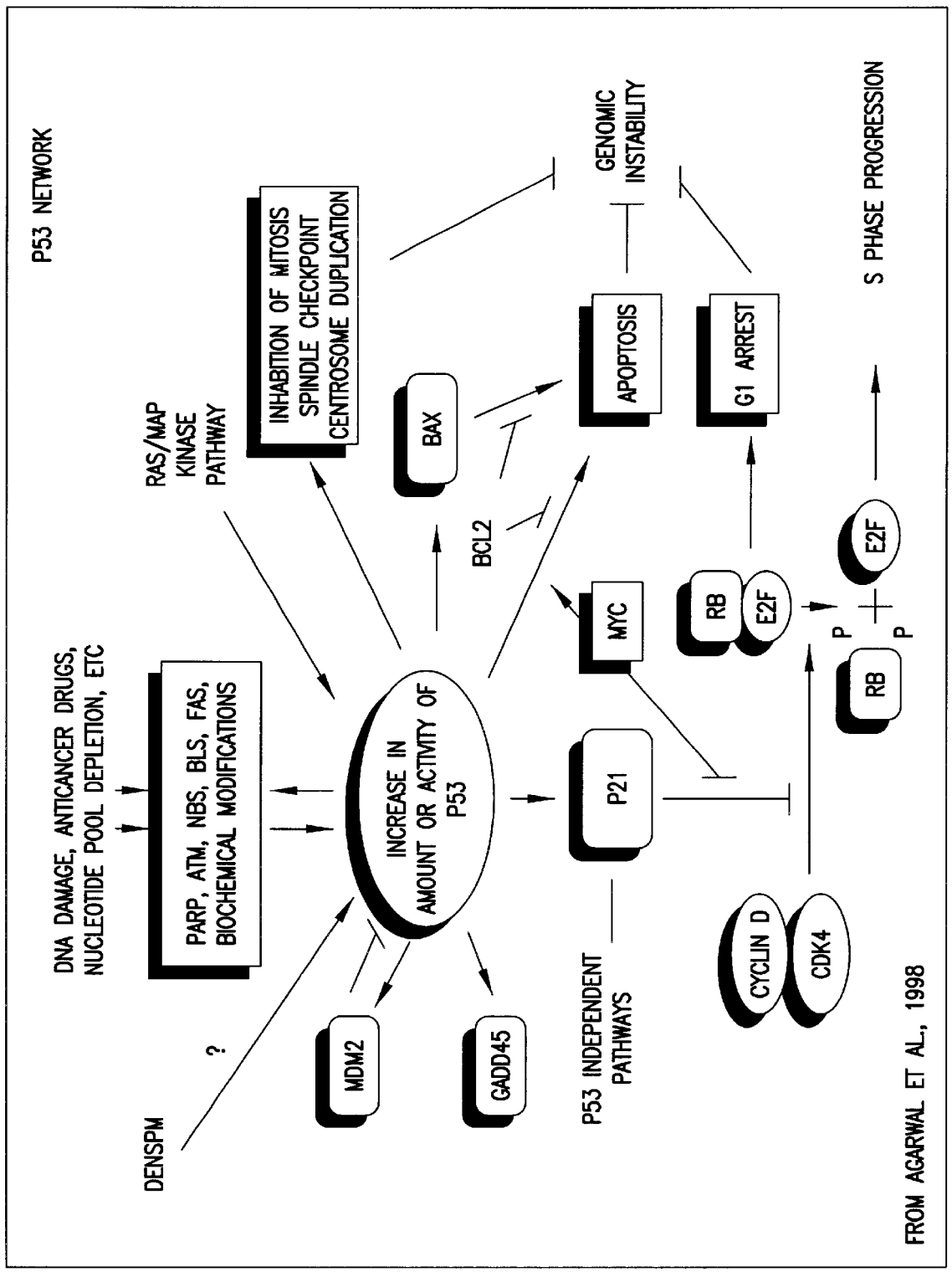
FIG. 7 is a flow chart showing the p53 network.

The p/53/p21 /Rb pathway is a well defined system for cell cycle regulation known to those of skill in the art. Briefly, p53 tumor suppressor gene controls cell growth by inducing cell cycle arrest. Cell growth regulation by p53 is effected, at least in part, by transcriptional activation of p21 gene, a cdk cell cycle inhibitor. p21, in turn, causes hypophosphorylation of the retinoblastoma protein (Rb), increased binding of Rb to the transcription factor E2F and reduced expression of S-phase specific genes. The p53 network is shown in FIG. 7. Additionally, the p53/p21/Rb pathway is described by Pagano, M. *Cell Cycle Control*, Soninger-Verlag, NY 1998. p 232, and Kramer et al., (1998) *Biochem. Soc. Trans.*, 26(4):6091614, the disclosures of which are hereby incorporated by reference.

Compounds

The invention provides a method for treating cancer, e.g., preferably a solid tumor, which includes administering to a patient suffering therefrom a therapeutically effective amount of a polyamine of the formula:

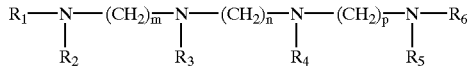

wherein:

$R_1$, $R_2$, $R_3$, $R_4$, $R_5$ and $R_6$ independently are hydrogen or $C_1$–$C_{12}$ alkyl; m, n and p are independently integers from 3 to 6;

or a pharmaceutically acceptable salt thereof, provided at least one of $R_1$, $R_2$, $R_5$ and $R_6$ is $C_1$–$C_{12}$ alkyl, in combination with at least one anticancer agent in unit dosage form. As used herein, the term "alkyl" denotes a hydrocarbon aliphatic group which is defined by the number of carbon atoms in the hydrocarbon chain. The chain may be either straight or branched. Examples of alkyl groups include methyl, ethyl, propyl, butyl, isobutyl, etc.

The method preferably is carried out employing a polyamine of the above formula wherein $R_1$ and $R_6$ both are $C_1$–$C_6$ alkyl, especially ethyl, and $R_2$, $R_3$, $R_4$ and $R_5$ are hydrogen. The method is ideally carried out utilizing a polyamine of the above formula where n, m and p independently are 3 or 4.

A particularly valuable compound employed in the method of the invention is the polyamine where m, n and p are 3. This compound is known as bis-ethylnorspermine or $N^1$, $N^{11}$-diethylnorspermine (DENSPM).

The compounds to be utilized in this invention are known and are readily prepared by any of several art-recognized methods. For example, Bergeron, U.S. Pat. Nos. 5,091,576 and 5,866,613 (the disclosures of which are incorporated herein by reference), describes a wide variety of polyamines such as those required for the present method. Synthesis of specific compounds to be utilized in this invention are provided by Bergeron, et al., in *J Med Chem.*, 31:1183–1190 (1988). A typical synthesis involves first monosulfonating all of the polyamine nitrogen atoms with p-toluenesulfonyl chloride, thereby leaving only the terminal nitrogens to be alkylated. The resulting sulfonamides were reacted with sodium hydride in an organic solvent such as dimethylsulfoxide, and reacted with an alkylating agent, for instance, methyl iodide, ethyl iodide, or the like. The terminally dialkylated sulfonamides thus formed are next hydrolyzed to remove sulfonyl protecting groups, for example, by reaction with sodium in liquid ammonia. The polyamines thus formed are purified by routine methods, for instance, by forming an acid addition salt such as the hydrochloride, and crystallizing it from common solvents. The salts can be utilized in the present method, or can be hydrolyzed with a base such as sodium hydroxide to give the free polyamine.

Formulations

While it is possible for the agents to be administered as the raw substances it is preferable, in view of their potency, to present them as a pharmaceutical formulation. The formulations, both veterinary and for human use, of the present invention comprise the agent, together with one or more acceptable carriers therefor and optionally other therapeutic ingredients. The carrier(s) must be "acceptable" in the sense of being compatible with the other ingredients of the formulation and not deleterious to the recipient thereof. Desirably, the formulations should not include oxidizing agents and other substances with which the agents are known to be incompatible. All methods include the step of bringing into association the agent with the carrier which constitutes one or more accessory ingredients.

The compounds of the present invention can be administered intravenously, transdermally, enterally, parenterally, intramuscularly, intranasally, subcutaneously, topically, intravesically orally or rectally. Examples of suitable formulations include tablets, dragees, gelatin capsules, suppositories, injectable or drinkable solutions, powders, pastes, ointments, jelly, waxes, and oils. The formulations may be prepared by any of the methods well known in the art of pharmacy. Examples of formulations can be found in Remington's Pharmaceutical Sciences, 15th Edition (1975), Mack Publishing Company, Easton, Pa. 18042. (Chapter 87: Blaug, Seymour). In general, the formulations are prepared by uniformly and intimately bringing into association the agent with the carrier(s) and then, if necessary, dividing the product into unit dosages thereof.

Preferably the formulation is suitable for parenteral administration. Such formulations preferably comprise sterile aqueous preparations of the agents which are preferably isotonic with the blood of the recipient. Suitable such carrier solutions include phosphate buffered saline, saline, water, lactated ringers or dextrose (5% in water). Such formulations may be conveniently prepared by admixing the agent with water to produce a solution or suspension which is filled into a sterile container and sealed against bacterial contamination. Preferably sterile materials are used under aseptic manufacturing conditions to avoid the need for terminal sterilization.

The formulations may optionally contain one or more additional ingredients including preservatives, such as methyl hydroxybenzoate, chlorocresol, metacresol, phenol and benzalkonium chloride. Such materials are of especial value when the formulations are presented in multi-dose containers.

Buffers may also be included to provide a suitable pH value for the formulation and suitable materials include sodium phosphate and acetate. Sodium chloride or glycerin may be used to render a formulation isotonic with the blood. If desired, the formulation may be filled into the containers under an inert atmosphere such as nitrogen or may contain an antioxidant, and are conveniently presented in unit dose or multidose form, for example, in a sealed ampule.

It will be appreciated that while the agents described herein form acid additional salts and carboxy acid salts the biological activity thereof will reside in the agent itself. These salts may be used in human and in veterinary medicine and presented as pharmaceutical formulations in the manner and in the amounts (calculated as the base) described hereinabove, and it is then preferable that the acid moiety be pharmacologically and pharmaceutically acceptable to the recipient. Examples of such suitable acids include (a) mineral acids: hydrochloric, hydrobromic, phosphoric, metaphosphoric, and sulphuric acids; (b) organic acids: tartaric acetic, citric, malic, lactic, fumaric, benzoic, glycolic, gluconic, gulonic, succinic and aryl-sulphonic, for example, p-toluenesulphonic acids.

The salts are prepared by contacting the free base form with a sufficient amount of the desired acid to produce either a mono or di, etc. salt in a conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the slats are otherwise equivalent to their respective free base forms for purposes of the invention.

Optimal dosage and regimen of the compound in a given mammalian host can be readily ascertained by those skilled in the art. It will be appreciated, of course, that the actual dose of compound will vary according to the particular composition formulated, the mode of application and the particular situs, host and disease being treated. Many factors that modify the action of the drug will be taken into account, including age, weight, sex, diet, time of administration, route of administration, rate of excretion, condition of the patient, drug combinations, reaction sensitivities and severity of the disease. Typically, the compound is administered at an amount within the range of about 50 to about 150 mg/kg/day.

Methods of Use

One aspect of the invention is directed towards a method of treating cancer in a mammal by administering a therapeutically effective amount of a polyamine, as above defined, in combination with an anticancer agent in unit dosage form to the mammal. The terms "treating", "treatment" and "therapy" as used herein refer to curative therapy, prophylactic therapy, and preventative therapy. The term "therapeutically effective amount" refers to the amount of compound which, when administered to a human or animal, prevents cancer, causes a reduction in cancer or inhibits the spread and proliferation of cancer. The therapeutically effective amount is readily determined by one of skill in the art following routine procedures. The term "cancer" refers to or describes a physiological condition in mammals that is typically characterized by unregulated cell growth. Frequently, cancer is characterized by a deficiency in p53 tumor suppressor protein. Examples of cancer include but are not limited to, carcinoma, including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. The term "in combination with" refers to treatment with the polyamine described herein and an anticancer agent either simultaneously or at such intervals that the drugs are simultaneously active in the body. The term "mammal" as used herein refers to any mammal classified as a mammal, including humans, cows, horses, dogs and cats. In a preferred embodiment of the invention, the mammal is a human. The term "anticancer agent" refers to agents which are used to treat cancer, including hydroxyurea, 5-azacytidine, 5-aza-2'-deoxycytidine, suramin, retinoids, hormones, biological response modifiers (such as interferon and hematopoietic growth factors), and conventional chemo- and radiation therapy or various combinations thereof. In one embodiment, the anticancer agent interacts with the p53/p21/Rb pathway. As used herein, the term "interacts with" refers to an anticancer agent that up-regulates or down-regulates an element of the pathway. For example, the anticancer agent may act as an agonist or antagonist that inhibits or stimulates activity of a receptor, nucleotide (DNA or RNA), enzyme, regulator protein or signalling molecule of the pathway. Examples of anticancer agents include, but are not limited to, cisplatin, camptothecins, doxorubicin, cyclophosphamide, or etoposide.

Treatment may be carried out by administering the polyamine and the anticancer agent concurrently but in separate unit dosage forms, preferably by parenteral administration. Alternatively, the polyamine and at least one anticancer agent may be administered together in a so-called "cocktail". The method of the present invention for treating cancer preferably is used in treating solid tumors, for example, non-small cell lung carcinoma, prostate carcinoma, renal carcinoma, colon carcinoma, ovarian carcinoma, pancreatic carcinoma, and melanoma.

A second aspect of the present invention is an in-vitro method for selecting patients for cancer treatment with a polyamine as defined above including the steps of isolating tumor cells from the patients; determining whether or not the tumor cells have a mutation in their p53 tumor suppressor gene; and treating patients having tumors containing the mutated p53 gene with a polyamine in combination with at least one anticancer agent as above defined.

Another embodiment is a method for treating a tumor in a mammal comprising the step of administering to the mammal an effective amount of a polyamine as described above in combination with an anticancer agent in unit dosage form.

The present invention also provides a method of inducing tumor cell apoptosis in a mammal comprising administering to the mammal a therapeutically effective amount of polyamine as described above in combination with an anticancer agent in unit dosage form. The term "apoptosis" is used in a broad sense and refers to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, FACS analysis, or DNA electrophoresis, all which are known in the art.

While not wishing to be bound by theory, it is believed that the polyamine of the invention introduces in cells treated therewith a prominent $G_1$ arrest and a less restrictive $G_2/M$ block followed by programmed cell death. It is believed that the $G_1$ arrest is induced via activation of the p53-p21-Rb pathway and is the end result of events preventing phosphorylation of Rb. Evidence suggesting that $G_1$ arrest occurs via the p53 response pathway includes: (a) the $G_1$ arrest and concomitant shift of Rb to a hypophosphorylated state is preceded by induction of p53 and p21; (b) induction of p21 is accompanied by increases in p21 mRNA as would be expected during transactivation by p53; and (c) cells which lack functional p53 fail to induce p53 or p21 and do not arrest in $G_1$.

It is believed that the following polyamine effects could serve to activate the appropriate sensors: (a) reduction of polyamine pools; (b) analog interactions with DNA and/or chromatin; (c) oxidative stress due to massive analog induction of spermidine/spermine $N^1$-acetyltransferase (SSAT); (d) generalized cellular stress and; (e) other pathways. These possibilities could be mediated by the analog indirectly by analog depletion of polyamine pools.

EXAMPLES

The effects of the polyamine herein described on growth, cell cycle and cell cycle proteins were examined in MALME-3M human melanoma cells and SK-MEL-28 human melanoma cells. MALME-3M cells express wild type p53 tumor suppressor gene (wt-p53). SK-MEL-28 cells express a mutant p53 tumor suppressor gene (mt-p53) having a cysteine to valine substitution at amino acid position 145, which is located in the DNA binding region of the molecule. (O'Connor et al., (1997) Cancer Res., 57:4285–4300).

Example 1

Cell Culture

MALME-3M human melanoma cells containing wt-p53 (American Tissue Type Culture Collection, Bethesda, Md.) and human SK-MEL-28 cells containing mt-p53 (American Tissue Type Culture Collection, Bethesda, Md.) were cultured as a monolayer in RPMI 1640 medium containing 10% Nu-Serum (Collaborative Research Products, Bedford, Mass.), 1 mM aminoguanidine, penicillin (50 units/ml) and streptomycin (50 µg/ml) as described by Kramer et al, J. Biol. Chem., 270:2124–32 (1995) and Kramer et al., Cancer Res., 57:5521–5527 (1997).

Example 2

Effect of Treatment with DENSPM on the Growth and Viability of MALME-3M Cells MALME-3M cells were cultured as described in Example 1. The cells were seeded by adding $1 \times 10^5$ cells to a T-25 vented cell culture flask. After 24 hours, the asynchronous cell cultures were treated with 10 µM $N^1$, $N^{11}$-diethylnorspermine (DENSPM) prepared by dissolving DENSPM in distilled water and sterilizing the solution by filtration through a 0.22 micron Millipore membrane. The cells were treated by continuous exposure to DENSPM for 6 days (i.e., the polyamine was added to the cell culture at T=0 and the culture was incubated for the desired amount of time). The number of viable MALME-3M cells were monitored electronically using a Model ZM Coulter Counter (Coulter Electronics, Hialeah, Fla.). Untreated MALME-3M cell cultures were used as controls.

Figure 1:
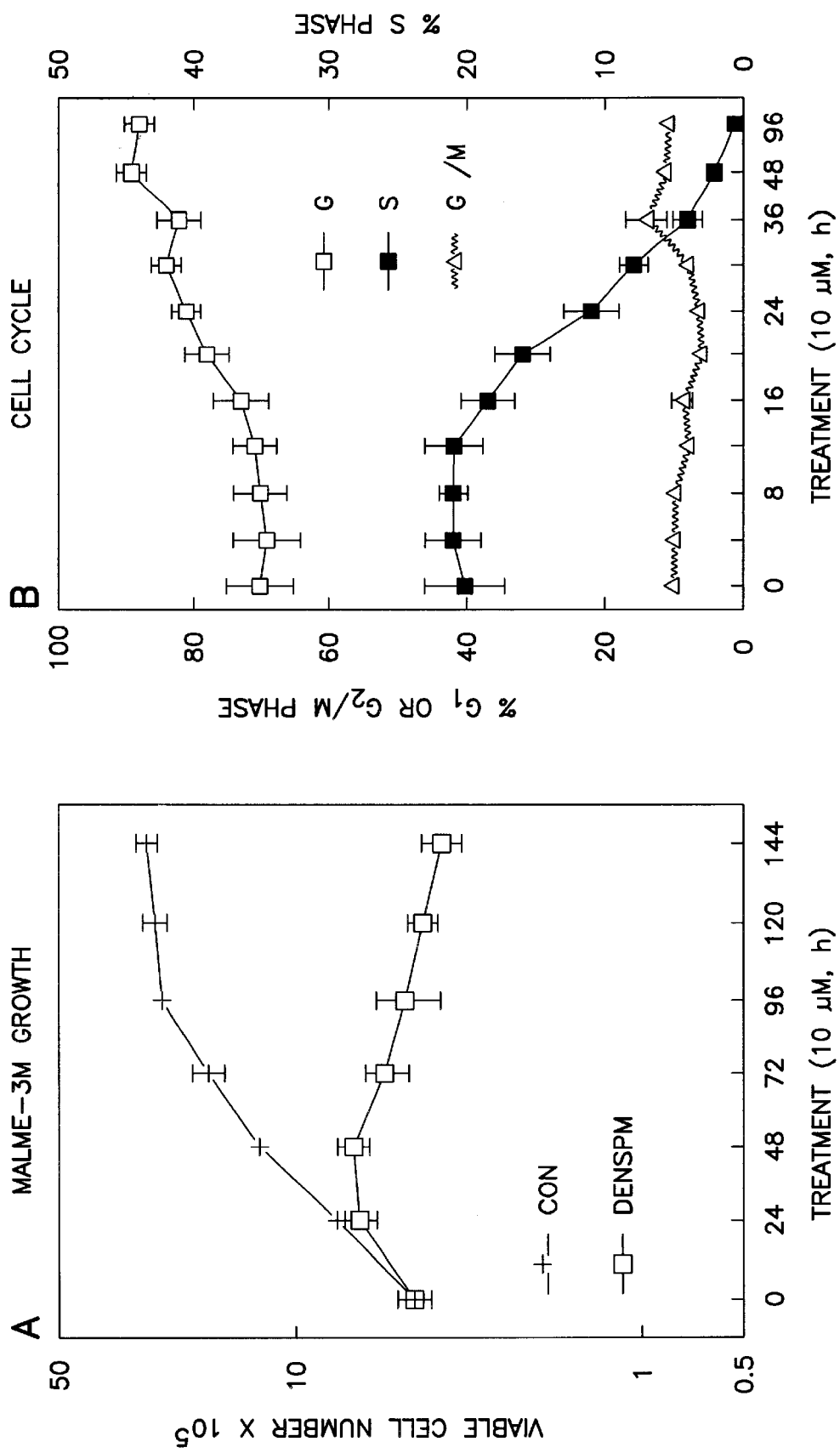
FIG. 1*a* is a graph showing the time-dependent effects of 10 μM DENSPM on asynchronous MALME-3M human melanoma cell growth.
FIG. 1*b* is a graph showing the time dependent effects of 10 μM DENSPM on asynchronous MALME-3M human melanoma cell cycle distribution.

The control MALME-3M cells demonstrated steady growth for 96 hours and then a plateau through 144 hours. In contrast, DENSPM treated MALME-3M cells demonstrated steady growth for the first 24 hours, then a plateau and then began to decline in number from 48 hours onwards. The time dependent effects of 10 µM DENSPM on asynchronous MALME-3M human melanoma cell growth are shown in FIG. 1, panel A. The data is expressed as a percentage of the initial seeding density in order to define $IC_{50}$ values as well as cytotoxic doses and is based on determinations from 3 separate experiments (mean±standard deviation).

Example 3

Effect of Treatment with DENSPM on the Cell Cycle of MALME-3M Cells

Asynchronous Cells

MALME-3M cells were cultured as described in Example 1 and treated with 10 µM DENSPM as described in Example 2. Cell cycle arrest was monitored using a FACScan flow cytometry unit (Becton Dickinson, San Jose, Calif.) according to the method of Krishan (1975) J. Cell Biol. 66:188–183. Untreated MALME-3M cell cultures were used as controls.

In MALME-3M cells, the onset of $G_1$ arrest began at about 16 hours after the cells were treated with DENSPM. $G_1$ arrest was reflected by an increase in $G_1$ phase cells and a decrease in the relative percentage of S-phase cells. Cells continued to accumulate in $G_1$ until 48 hours when the proportion of cells remaining in S-phase declined from an original level of 20% to less than 2%. Despite this marked loss in S-phase cells, the proportion of cells in $G_2/M$ phase remained about 10%, indicating co-existence of a $G_2/M$ block.

The results are shown in FIG. 1, panel B. The left axis represents the relative percentage of total cells in $G_1$ and $G_2/M$ phases of the cell cycle. The right axis represents the relative percentage of total cells in S-phase of the cell cycle. The data in is based on determinations from 3 separate experiments (mean±standard deviation).

Serum Synchronized Cells

Figure 2:
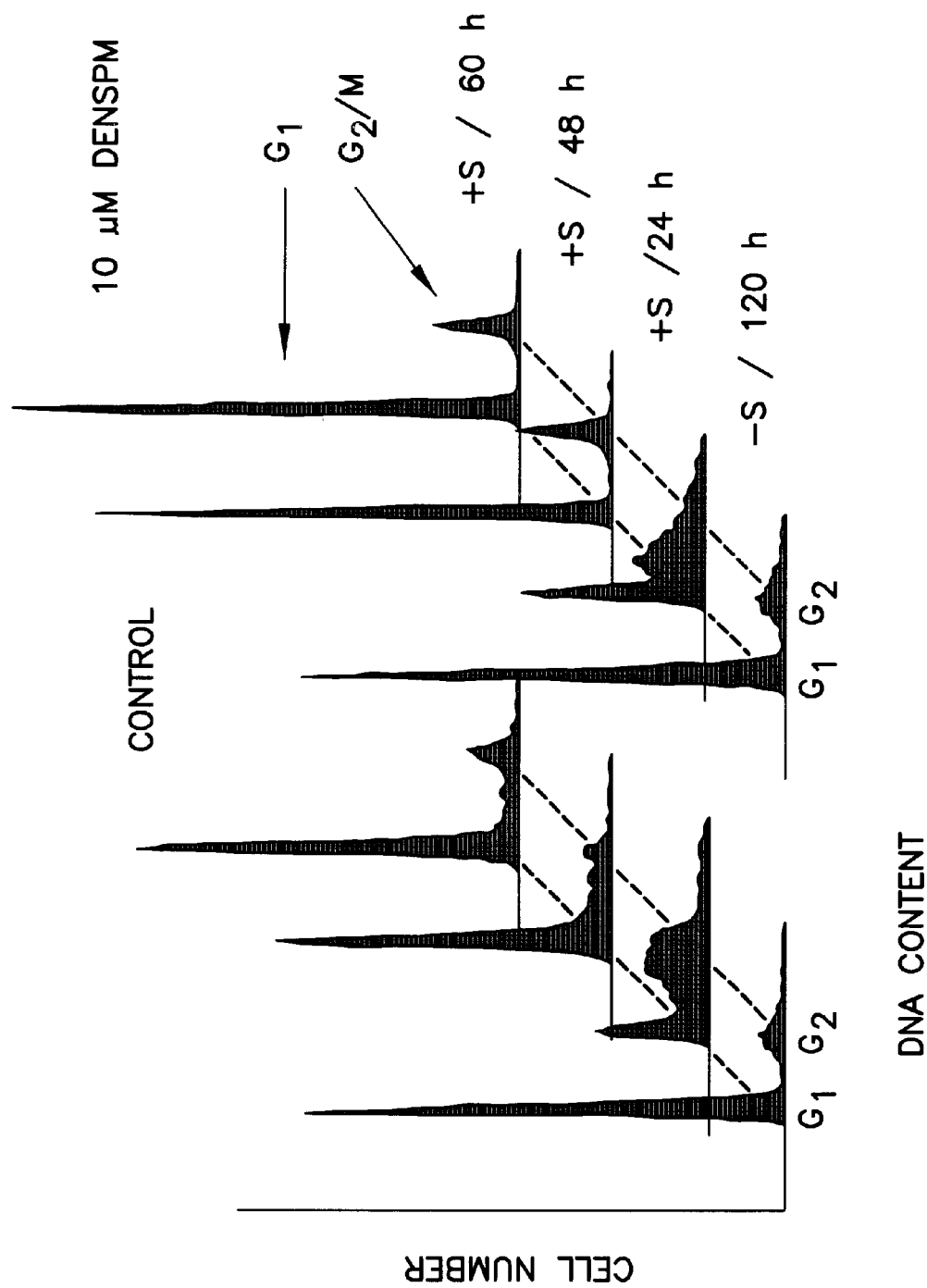
FIG. 2 is a graph showing the effects of 10 μM DENSPM on synchronized MALME-3M human melanoma cell cycle distribution.

Cell cycle arrest of serum synchronized MALME-3M cells was also monitored using flow cytometry. MALME- 3M cells were synchronized in $G_0/G_1$ by replacing cell culture media containing 10% NuSerum (see Example 1) with media lacking NuSerum and incubating the cultures for 120 hours. The synchronized cells were released by the addition of 10% NuSerum (control culture) or 10% NuSerum plus 10 μM DENSPM. The cells were then grown continuously in the presence of serum (control) or DENSPM for up to 96 hours. The untreated cells (control) re-established an asynchronous profile (i.e., progressed through the cell cycle) by 60 hours. DENSPM-treated cells accumulated in the $G_1$ and $G_2/M$ phases of the cycle but not in S phase. The results are shown in FIG. 2.

These results provide evidence for a DENSPM induced $G_1$ and $G_2/M$ cell cycle block in MALME-3M cells. The data are representative of two separate experiments.

Example 4

Effect of Treatment with DENSPM or Spermine (a Natural Polyamine) on Cell Cycle of MALME-3M Human Melanoma Cells and SK-MEL-28 Human Melanoma Cells MALME-3M human melanoma cells were cultured as described in Example 1 and treated continuously with 10 μM DENSPM or 10 μM spermine (SPM) for 48 hours. SK-MEL-28 cells were also cultured as described in Example 1 and treated with 10 μM DENSPM for 24 hours. Untreated cells were used as a control.

The effect of DENSPM and spermine on cell growth was monitored using a Coulter Counter (see Example 2). The effect on cell cycle was monitored by flow cytometry as described in Example 3. The results are shown in Table 1, below.

TABLE 1

DENSPM and Spermine Effects on Cell Cycle in MALME-3M and SK-MEL-28 Human Melanoma Cells*.

| Cell Line | Treatment (48 hours) | % Control Growth | % Total Cells at 48 hours | | |
|---|---|---|---|---|---|
| | | | $G_1$ | S | $G_2/M$ |
| MALME-3M | Control | 100 | 64 | 26 | 10 |
| (wt-p53) | 10 μM DENSPM | 54 | 88 | 2 | 10 |
| | 10 μM SPM | 96 | 67 | 23 | 10 |
| SK-MEL-28 | Control | 100 | 60 | 25 | 15 |
| (mt-p53) | 10 μM DENSPM | 0 | 74** | 17** | 9** |

*Data represent mean values from at least three separate experiments with S.D. < 10%
**Cell cycle data for attached SK-MEL-28 cells was obtained following 24 hours treatment; 48 hour treatment was profoundly toxic.

As shown in Table 1, above, spermine had no effect (as compared to the control cells) on the growth or cell cycle of MALME-3M cells. In contrast, DENSPM substantially reduced MALME-3M cell growth, increased the percentage of cells in $G_1$ phase and decreased the percentage of cells in S phase of the cell cycle. For the SK-MEL-28 cells, DENSPM substantially arrested cell growth. A reliable cell cycle was not possible at 48 hours since most cells were dead. At 24 hours, neither the modest increase in $G_1$ cells (which could not be separated from apoptotic cells) nor the similarly modest decrease in S phase cells were considered sufficiently significant to assign a $G_1/S$ phase arrest. Thus, while wt-p53 containing MALME-3M cells underwent a clear $G_1$ arrest in response to DENSPM, SK-MEL-28 cells appeared to undergo a more cytotoxic response in the absence of a distinguishable $G_1$ arrest.

Example 5

Effect of DENSPM or Spermine on Polyamine Metabolism in MALME-3M and SK-MEL-28 Human Melanoma Cells MALME-3M human melanoma cells were cultured as described in Example 1 and treated with 10 μM DENSPM or 10 μM spermine (SPM) as described in Example 4. SK-MEL-28 cells were also cultured as described in Example 1 and treated with 10 μM DENSPM as describe in Example 4. Untreated cells were used as a control.

After treatment with DENSPM or spermine, biochemical parameters including polyamine enzymes activity, polyamine pools and analog accumulation were monitored as described by Kramer et al, *J. Biol. Chem.*, 270:2124–32 (1995) and Kramer et al., *Cancer Res.*, 57:5521–5527 (1997). Polyamine enzyme activity was monitored for ornithine decarboxylate (ODC); S-adenosylmethionine decarboxylase (SAMDC); and spermidine/spermine $N^1$-acetyltransferase (SSAT). Polyamine pools was monitored for putrescine (Put); spermidine (Spd); and spermine (Spm). The results are shown in Table 2, below.

TABLE 2

DENSPM and Spemine Effects on Polyamine Metabolism in MALME-3M and SK-MEL-28 Human Melanoma Cells*.

| | | | Polyamine Enzyme Activities | | | | | |
|---|---|---|---|---|---|---|---|---|
| Cell Line | Treatment | % Growth Control | ODC (pmol/hr/mg protein) | SAMDC** (pmol/hr/mg protein) | SSAT (pmol/min/mg) | Polyamine Pools (pmol/10^6 cells) | | |
| | | | | | | Put | Spd | Spm |
| MALME-3M | Control | 100 | 1605 | 226 | 40 | 895 | 2095 | 1875 |
| (wt-p53) | 10 μM DENSPM | 83 | 30 | 40 | 26,220 | 205 | 60 | 285 |
| | 10 μM SPM | 97 | 175 | 20 | 210 | <5 | 470 | 2430 |

TABLE 2-continued

DENSPM and Spemine Effects on Polyamine Metabolism in
MALME-3M and SK-MEL-28 Human Melanoma Cells*.

| | | | Polyamine Enzyme Activities | | | Polyamine Pools (pmol/10$^6$ cells) | | |
|---|---|---|---|---|---|---|---|---|
| Cell Line | Treatment | % Growth Control | ODC (pmol/hr/mg protein) | SAMDC** (pmol/hr/mg protein) | SSAT (pmol/min/mg) | Put | Spd | Spm |
| SK-MEL-28 (mt-p53) | Control | 100 | 660 | 190 | 35 | 20 | 605 | 2005 |
| | 10 μM DENSPM | 26 | 5 | 25 | 31,920 | 70 | 20 | 105 |

*Data represent mean values from three separate experiments with S.D. < 10%

The growth response of MALME-3M and SK-MEL-28 cells treated with DENSPM or spermine, shown in Table 2, follow the results shown in Table 1.

Despite different cellular responses to DENSPM, both MALME-3M and SK-MEL-28 cell lines underwent an early and near total reduction in polyamine pools. As shown in Table 2, natural polyamine pools were depleted after only 24 hours treatment. The depletion of polyamine pools in both MALME-3M and SK-MEL-28 cells is likely due to down regulation of the polyamine biosynthetic enzymes, ornithine decarboxylate (ODC) and S-adenosylmethionine decarboxylase (SAMDC), and a potent induction of the polyamine catabolic enzyme spermidine/spermine N$^1$-acetyltransferase (SSAT). SSAT activity increased from about 40 to greater than 25,000 pmol/min/mg in both MALME-3M and SK-MEL-28 cells. The similarity in polyamine metabolic responses to DENSPM in MALME-3M cells and SK-MEL-28 cells indicates that their differential growth response is likely to be determined by differences in the genetic composition of these two cell lines.

Example 6

Effect of SSAT Induction and/or Polyamine Depletion in the Apoptotic Response of SK-MEL-28 cells The effect of SSAT induction and/or polyamine depletion in the apoptotic response seen in SK-MEL-28 cells was investigated. Since there are no known specific or effective inhibitors of SSAT and since specific inhibitors of polyamine biosynthesis only partially deplete polyamine pools, we compared the relative effects of DENSPM to a series of three DENSPM analogs that accumulate to relatively the same levels in cells, similarly suppress ODC and SAMDC and deplete polyamines but differ in their abilities to induce SSAT. Porter et al., (1 991) *Cancer Res.*, 51:3715–3720; Pegg et al., (1989) *J. Biol. Chem.*, 264:11744–111749; and Kramer et al., (1997) *Cancer Res.* 57:5521–5527. The structures of these analogs are shown in Table 3, below.

Apoptosis was initially suggested by a loss in cell number as detected by growth kinetic analysis as described in Example 3. Enzyme activity and polyamine pools were measured as described in Example 5.

TABLE 3

Structures of polyamine analogs

| Analog | Abbreviation | Structure** |
|---|---|---|
| N$^1$,N$^{11}$-diethylnorspermine | DENSPM (DE-333) | CH$_3$CH$_2$NH(CH$_2$)$_3$NH(CH$_2$)$_3$NH(CH$_2$)$_3$NHCH$_2$CH$_3$ |
| N$^1$,N$^{12}$-diethylspermine | DESPM (DE-343) | CH$_3$CH$_2$NH(CH$_2$)$_3$NH(CH$_2$)$_4$NH(CH$_2$)$_3$NHCH$_2$CH$_3$ |
| 3,7,12,17-tetraazanonadecane* | DE-443 | CH$_3$CH$_2$NH(CH$_2$)$_4$NH(CH$_2$)$_4$NH(CH$_2$)$_3$NHCH$_2$CH$_3$ |
| N$^1$,N$^{14}$-diethylhomospermine | DEHSPM (DE-444) | CH$_3$CH$_2$NH(CH$_2$)$_4$NH(CH$_2$)$_4$NH(CH$_2$)$_4$NHCH$_2$CH$_3$ |

*also called N$^1$,N$^{13}$-diethyl(aminopropyl)homospermidine
**Note that these tetra-amine homologs differ only in the intra-amine carbon distances.

It was theorized that if SSAT induction contributed to apoptosis, differential enzyme induction should produce a differential apoptotic response. In contrast, if polyamine depletion was the determining event, apoptosis should be similarly affected by all four analogs. The results are shown in Table 4 and FIG. 6.

TABLE 4

Relative DENSPM Analog Effects on Polyamine Metabolism in SK-MEL-28 Cells*.

| Treatment (24 hours) | % Control Growth | Enzyme Activities** | | Polyamine Pools (pmol/10$^6$ cells) | | | |
|---|---|---|---|---|---|---|---|
| | | ODC | SSAT | Put | Spd | Spm | Analog |
| Control | 100 | 950 | 35 | 40 | 975 | 3170 | 0 |
| DE-444 | 97 | 14 | 930 | 20 | 120 | 1015 | 5950 |
| DE-443 | 77 | 32 | 5215 | 20 | 70 | 500 | 5610 |
| DE-343 | 59 | 23 | 9470 | 60 | 60 | 200 | 5830 |
| DENSPM (DE-333) | 30 | 37 | 31920 | 115 | 45 | 190 | 7710 |

TABLE 4-continued

Relative DENSPM Analog Effects on Polyamine Metabolism in SK-MEL-28 Cells*.

| Treatment (24 hours) | % Control Growth | Enzyme Activities** | | Polyamine Pools (pmol/10⁶ cells) | | | |
|---|---|---|---|---|---|---|---|
| | | ODC | SSAT | Put | Spd | Spm | Analog |
| DENSPM plus MDL-72527 | 45 | nd | nd | 40 | 40 | 360 | 5900 |

Figure 6:
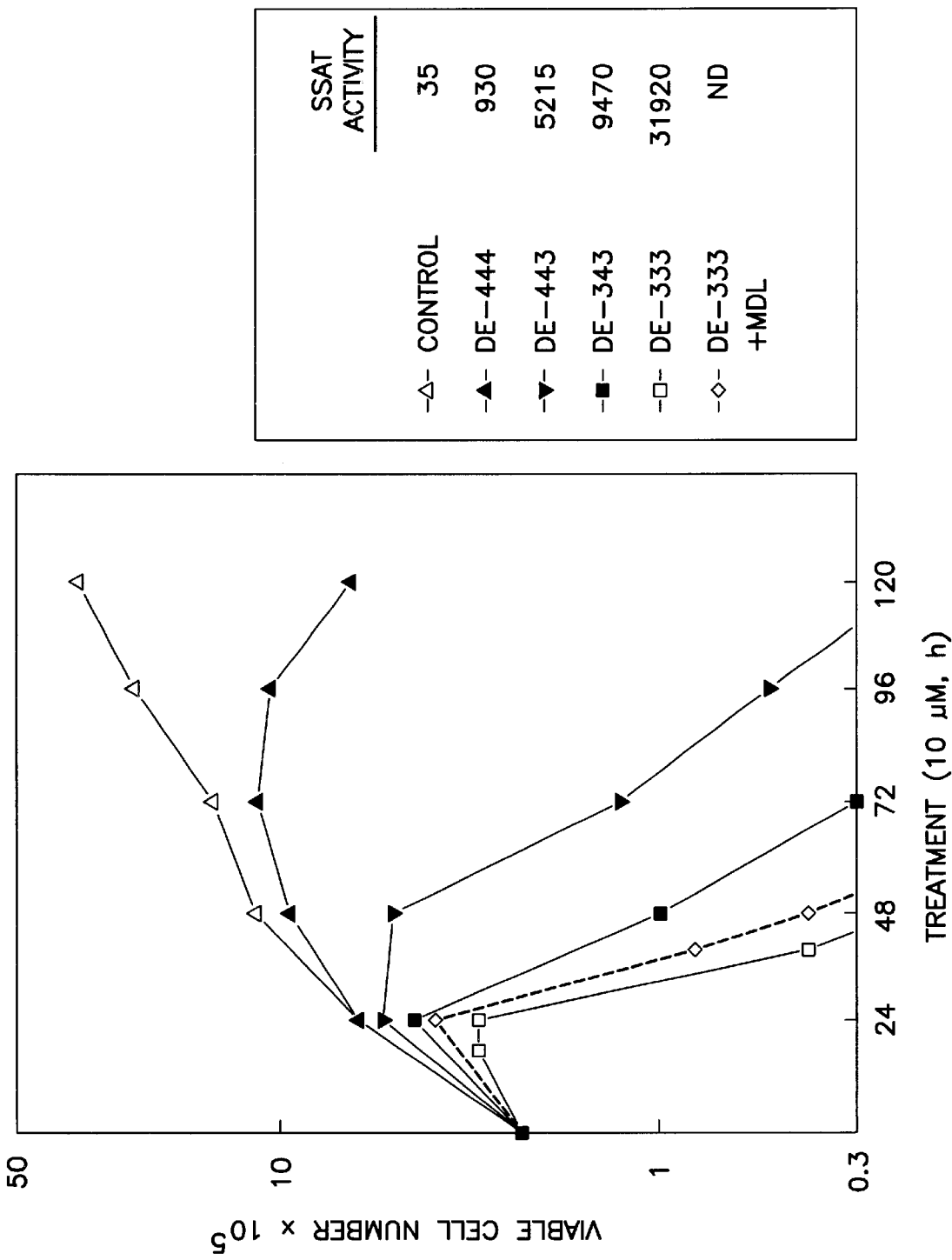
FIG. 6 is a graph showing the differential effects of polyamine analogs on spermidine/spermine $N^1$-acetyltransferase (SSAT) induction and cell growth and/or apoptosis in SK-MEL-28 human melanoma cells.

*Data represent mean values from three separate experiments with S.D. < 10%
**Units for ODC, pmol/hr/mg protein, SSAT pmol/min/mg protein
nd = not determined FIG. 6 shows differential effects of DENSPM (DE-333) and the three homologs on SSAT induction and cell growth and/or apoptosis in SK-MEL-28 cells. Data to the right of the growth panel represent SSAT activity at 24 hours in pmol/mg/min.

$N^1$, $N^{14}$-diethylhomospermine (DE-444) increased SSAT activity to 930 pmol/min/mg and produced a cytostatic response. DENSPM induced SSAT to 31,920 pmol/min/mg and resulted in a massive and rapid apoptotic response. $N^1$, $N^{12}$-diethylspermine (DE-343) increased SSAT activity 10 times higher than DE-444 and only about 3 fold less than DENSPM (9,470 pmol/min/mg) and produced an apoptotic response similar to that by DENSPM with a 24 hour delay. DE-443 induced an intermediate level of enzyme activity (5,215 pmol/min/mg) and produced an apoptotic response with a 48 hour delay. The results demonstrate that SSAT induction contributes to apoptosis. Consequently, all four analogs are potentially suitable as anticancer agents.

Spermine pools were differentially affected by the analogs in a manner correlative to SSAT induction. For example, DE-333 produced a 95% decrease in spermine pools, DE-444, a 65% decrease and the other analogs, intermediate effects. This correlation demonstrates that spermine depletion caused by SSAT induction may play a role in mediating apoptosis.

Confirmation of apoptosis was carried out by quantitative morphologic analysis using attached and detached MALME-3M and SK-MEL-28 cell populations for 24, 48 and 96 hour incubations with 10 μM DENSPM using methods described by Kramer et al., *Cancer Res.*, 57:5521–5527 (1997). The methods include morphology following cytospin and hematoxylin and eosin staining as well as immunocytchemical staining performed according to the procedure in the ApopTag™ Plus Kit (Oncor, Gaithersburg, Md.).

Example 7

Analysis of Apoptosis using Nuclear Magnetic Resonance Spectra

Apoptosis of MALME-3M and SK-MEL-28 cells due to treatment with 10 μM DENSPM was quantified using proton nuclear magnetic resonance (NMR) spectroscopy. NMR was used to detect membrane phospholipid spectral intensity changes which correlate with surface expression of phosphatidylserine, an early marker of apoptosis. Changes in methylene and methyl peaks were detected by the annexin V assay described by Blankenberg et al., *Blood*, 89:3778–3786 (1997).

Figure 3:
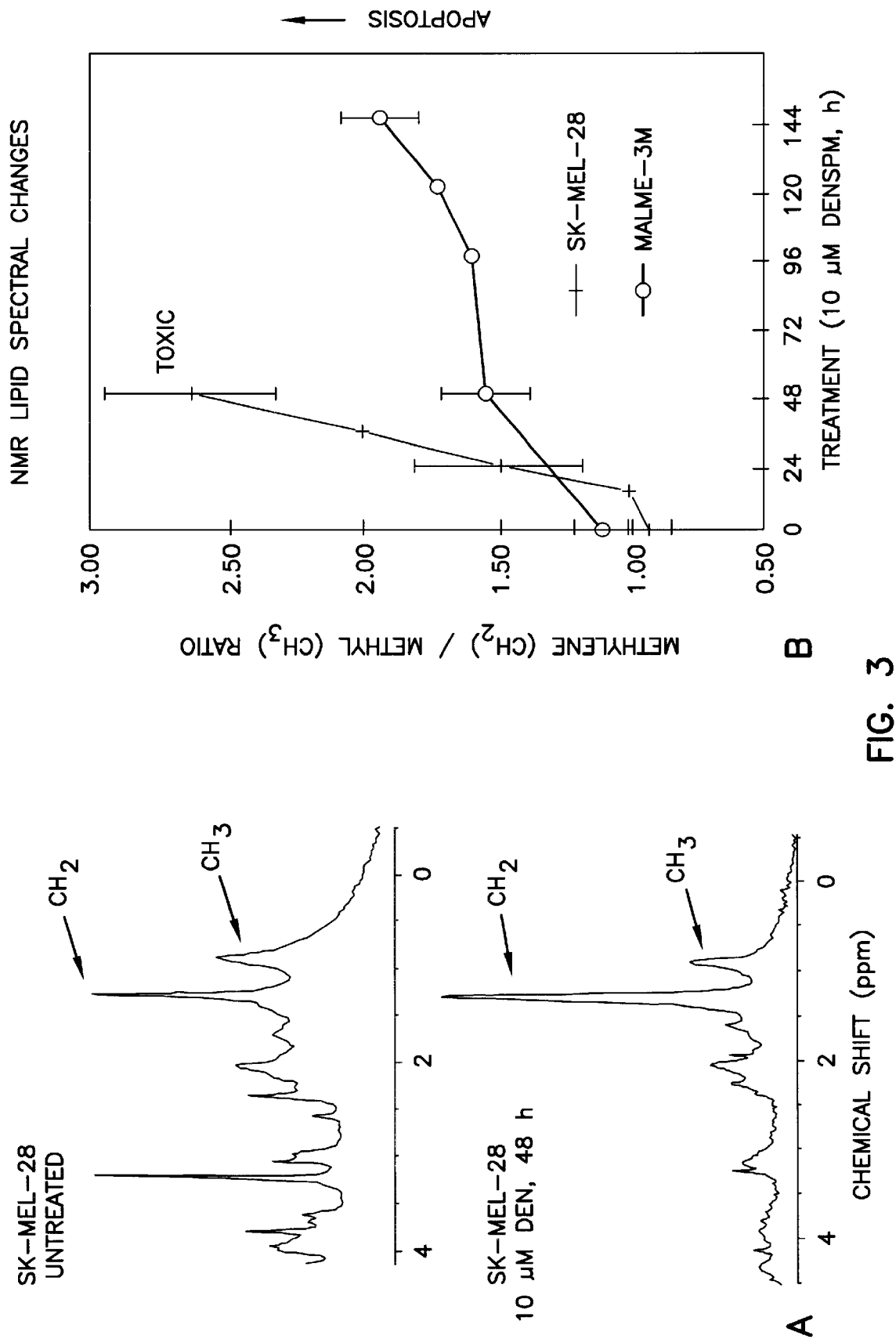
FIG. 3*a* is a nuclear magnetic resonance (NMR) trace showing the effects of 10 μM DENSPM on the membrane lipids of SK-MEL-28 human melanoma cells.
FIG. 3*b* is a graph showing the effect of 10 μM DENSPM on the membrane lipids of SK-MEL-28 human melanoma cells and MALME-3M human melanoma cells as detected by nuclear magnetic resonance (NMR).

Intensity changes in membrane lipids was measured using NMR after 72 hours of continuous treatment with 10 μM DENSPM. The results are shown in FIG. 3. Panel A shows representative NMR spectral tracings for untreated (control) and DENSPM-treated SK-MEL-28 cells. Panel B shows the time dependent increase in methylene/methyl ratio for the two cell types. The SK-MEL-28 cells undergo a rapid spectral ratio change which correlates with the massive cell loss seen in FIG. 4. Maximal cell death occurred by 48 hours in SK-MEL-28 cells. The data represent the mean ratio±standard deviation.

For perspective, a methylene to methyl spectral ratio of about 1 is typical of untreated cells while a ratio of about 3 is the maximum attainable with most apoptotic responses. Thus, the ratio of 2.6 observed with DENSPM-treated SK-MEL-28 cells at 48 hours represents a full scale response.

Example 8

Western Blot Assays

MALME-3M and SK-MEL-28 cells cultured as described in Example 4 were treated with 10 μM DENSPM for 0 to 48 hours. Western blot analysis of cell cycle regulatory proteins, including p53, p21, p27, ppRb, pRb, cyclin $D_1$ and PCNA was performed following the procedure described by Fogel-Petrovic et al. in *Molec. Pharm*, 52:69–74 (1997); and *Biochemistry*, 35:14436–14444 (1996). Antibodies used for detecting the proteins were obtained commercially as follows: p53 from Santa Cruz Biotechnology, Inc. (Santa Cruz, Calif.); PCNA and Cyclin $D_1$ from Oncogene Research Products (Cambridge, Mass.); Rb and p21 from PharMigen (San Diego, Calif.); p27 from Transduction labs (Lexington, Ky.) and β-actin (used to correct for variations in loading) from Sigma Chemical Co. (St. Louis, Mo.). Western blot analysis of each of these proteins was performed at least three times.

An increase in wild type p53 began at about 12 hours and reached about a maximum at 30 hours before declining. An increase in the cdk inhibitor p21 began at about 12 hours also peaked at a maximum at 30 hours. Despite the increase in p21, protein levels of PCNA (which can be inhibited by p21; Luo et al., (1995) *Nature*, 375:159–161) were unaffected by DENSPM treatment. Another cdk inhibitor, p27, displayed a similar profile as p21 but the level of induction was much less, reaching a maximum of about 1.5 fold at 24 to 30 hours. According to densitometric quantitation and normalization to β-actin, the 30 hour peak in p53 and p21 represents a 10 and a 5 fold increase (relative to zero treatment time) in protein, respectively.

The Western blot analysis revealed a shift of the retinoblastoma protein (Rb) from a hyperphosphorylated state (ppRb) to a hypophosphorylated state (pRb). The shift began with the appearance of the hypophosphorylated Rb (pRb) protein band at about 16 hours. By 48 hours, pRb was the only species. This time-dependent shift in Rb status correlated closely with the onset of $G_1$ arrest (see FIG. 1). There was no comparable change in the levels of the related pocket protein p130 or the two markers of $G_1$, cyclin D1 and cyclin E, which tended to remain relatively constant throughout the 48 hour time course (data not shown). These findings demonstrate that the $G_1$ arrest induced by DENSPM in MALME-3M cells closely correlates on a temporal basis by a rapid and substantial induction of p53 and p21 cell cycle proteins. Thus, the $G_1$ arrest appears to be selectively mediated via the p53/p21/Rb response.

Figure 4:
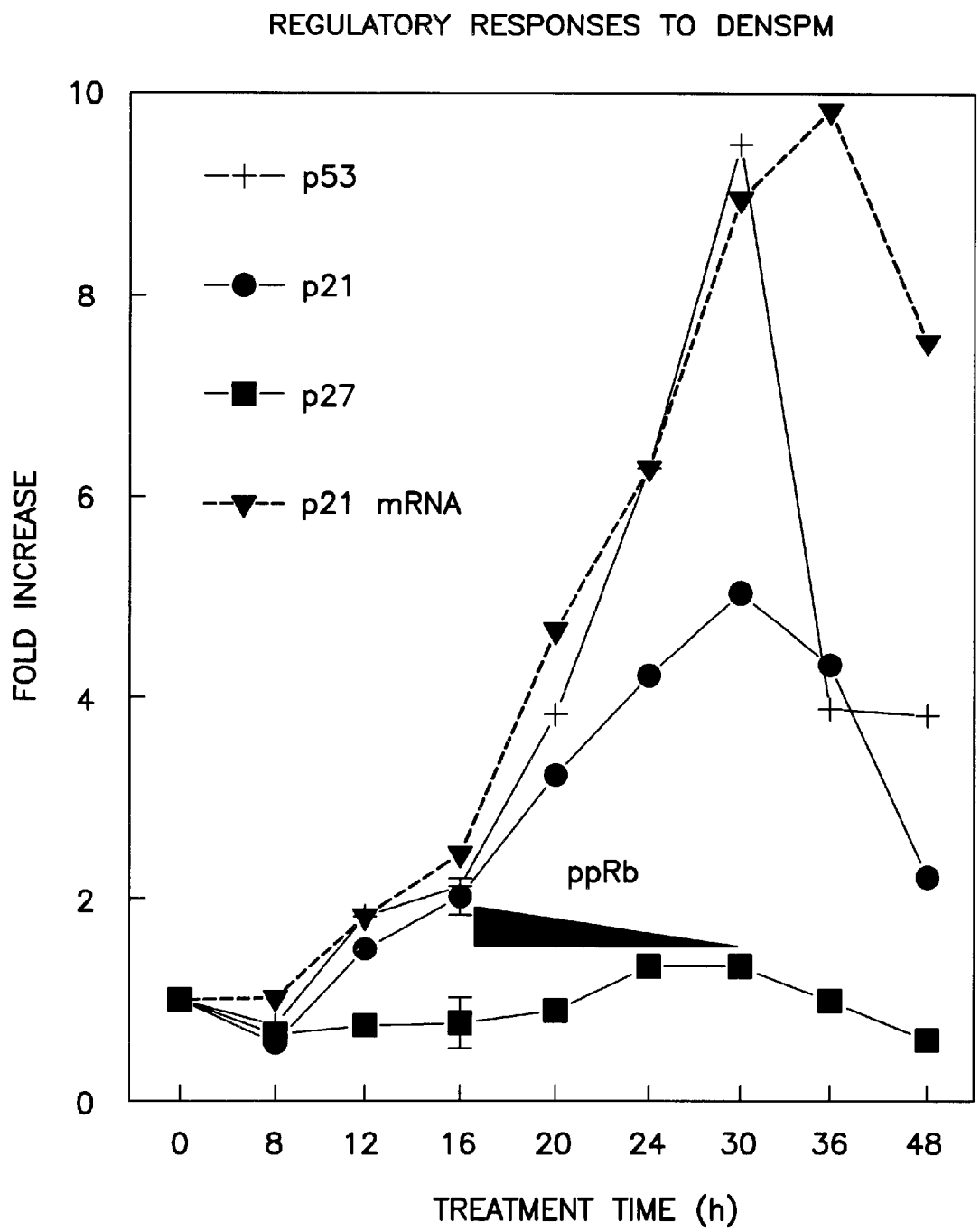
FIG. 4 is a graph showing the relative time-dependent changes in cell cycle regulatory protein expression and p21 mRNA levels in MALME-3M cells treated with 10 μM DENSPM. The dark wedge indicates the time frame for the conversion of hyperphosphorylated Rb protein (ppRb) to hypophosphorylated Rb protein (pRb).

FIG. 4 shows the relative changes in cell cycle regulatory protein expression and p21 mRNA levels during treatment of MALME-3M cells with DENSPM. The dark wedge indicates the time frame for the conversion of hyperphosphorylated Rb protein (ppRB) to hypophosphorylated Rb protein.

Example 9

Northern Blot Assays of Cell Cycle Regulatory Gene Expression

Asynchronously growing MALME-3M cells were treated for 0 to 48 hours with 10 μM DENSPM as described in Example 2. Northern blots were used to detect mRNA for p53 and p21. The Northern blot procedure is described by Fogel-Petrovic et al. in *Molec. Pharn*, 52:69–74 (1997); and *Biochemistry*, 35:14436–14444 (1996). cDNA probes used in Nothern blot hybridization of p21 and p53 mRNA were obtained, respectively, from Dr. Bert Vogelstein (Johns Hopkins Oncology Center, Baltimore, Md.; El-Deiry et al., *Cell*, 75:817–825) and from Dr. Stephen Friend (Seattle, Wash.; Ishioka et al., *Oncogene* 10:1485–1492 (1995)). The relative increase in mRNA with analog treatment was normalized to the glyceraldehyde-3-dehydrogenase (GAPDH) signal to account for lane loading differences. The results are shown in FIG. 4.

Northern blot analysis showed that p53 mRNA remained constant during treatment with DENSPM. This indicates that the rise in p53 is probably due to post-transcriptional mechanisms. As shown in FIG. 4, p21 mRNA began to increase at 12 hours and continued to rise to about 20 fold at 48 hours which (well beyond the p21 protein peak seen at 30 hours). Thus, the p21 mRNA response coincided with the rise in p53 protein and the initial increase in p21 protein. The data demonstrate that $G_1$ arrest induced by DENSPM is probably mediated via the p53/p21/Rb checkpoint in tumor cells which retain p53 suppressor gene function.

Example 10

Figure 5B:
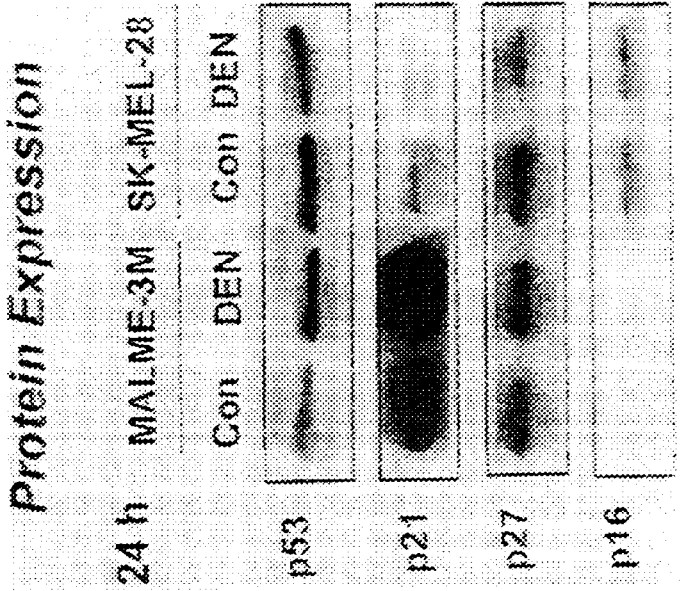
FIG. 5b is a photograph of a gel showing the effect of 10 µM DENSPM on MALME-3M and SK-MEL-28 cell cycle regulatory proteins.
Figure 5A:
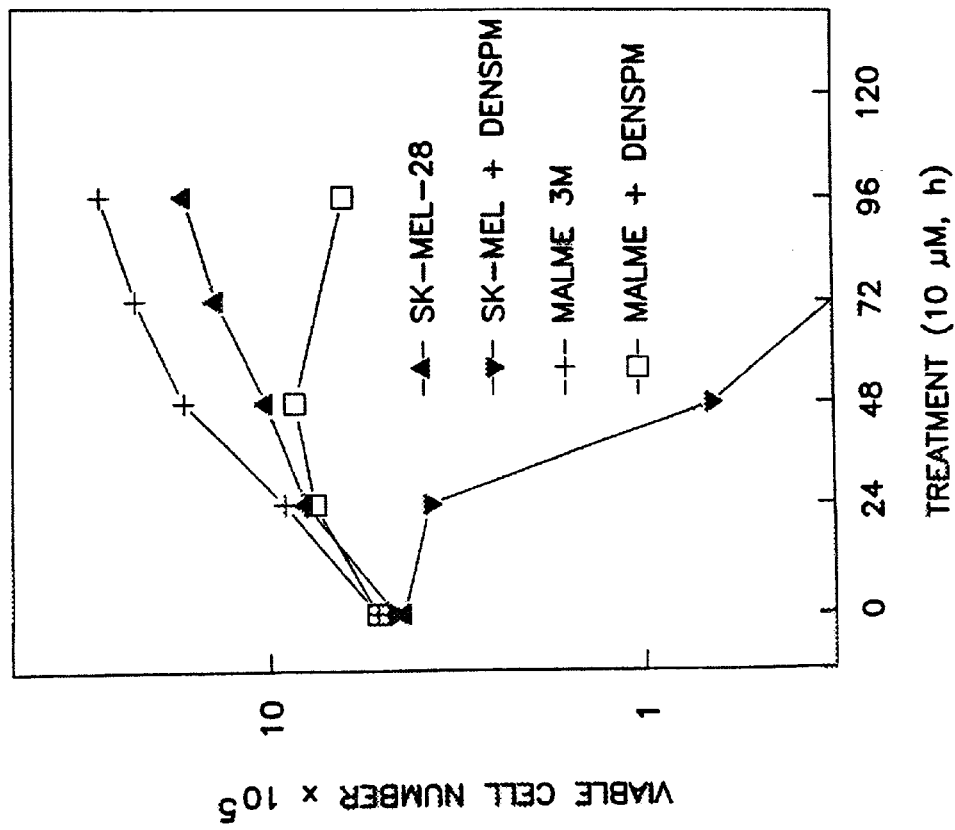
FIG. 5*a* is a graph showing the effect of 10 μM DENSPM on MALME-3M and SK-MEL-28 human melanoma cell growth.

Comparison of Protein and Cellular Responses to DENSPM in MALME-3M and SK-MEL-28 Cells The effects of 10 μM DENSPM on MALME-3M and SK-MEL-28 cell growth and cell cycle regulatory proteins were determined as described in Examples 2 and 3, respectively. The results are shown in FIG. 5. Panel A is a comparison of the effects of DENSPM on cell growth. Panel B is a comparison of cell cycle regulatory proteins. SK-MEL-28 cells lack the initial growth arrest seen in MALME-3M cells and instead exhibit a rapid cytotoxic response. Additionally, compared to MALME-3M cells, the level of p21 protein in SK-MEL-28 cells was reduced and was not induced with treatment. p16 was present in SK-MEL-28 cells and did not change with treatment. In contrast, p16 was not detectable in MALME-3M cells. Data is representative of at least two experiments.

These results indicate that there is no induction of p53 at 24 hours and only barely detectable basal levels of p21 in SK-MEL-28 cells. Similarly, cdk inhibitors p16 and p27 in SK-MEL-28 cells were also not increased by DENSPM. Thus, unlike MALME-3M cells which seem to undergo a sustained $G_1$ arrest before undergoing a modest apoptosis, SK-MEL-28 cells bypass $G_1$ arrest and rapidly proceed to a near-total programmed cell death response. This response is apparently not p53 dependent.

Although SK-MEL-28 and MALME-3M cells are similar in their ability to induce SSAT in response to DENSPM, SK-MEL-28 cells are deficient in p53 suppressor gene function and MALME-3M cells are not. Thus, MALME-3M cells develop a $G_1$ arrest via the p53/p21/Rb pathway in response to DENSPM while SK-MEL-28 cells are unable to mount such a response and instead, undergo immediate apoptosis. This finding is consistent with the theory that the p53/p21/Rb pathway delays or prevents apoptosis. Thus, cells lacking functional p53 capabilities are more susceptible to the cytotoxic effects of DENSPM.

The above specification, examples and data provide a complete description of the manufacture and use of the composition of the invention. Since many embodiments of the invention can be made without departing from the spirit and scope of the invention, the invention resides in the claims hereinafter appended. All references cited herein are hereby incorporated by reference.

We claim:

1. A method of treating cancer in a patient comprising:

determining whether the cancer comprises tumor cells which are deficient in p53; and administering a polyamine of the formula:

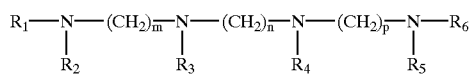

wherein:

$R_1$, $R_2$, $R_3$, $R_4$, $R_5$ and $R_6$ independently are hydrogen or $C_1$–$C_{12}$ alkyl; m, n and p are independently integers from 3 to 6; and at least one of $R_1$, $R_2$, $R_5$, and $R_6$ is $C_1$–$C_{12}$ alkyl.

2. The method according to claim 1, wherein the polyamine is administered in combination with at least one other anticancer agent in unit dosage form.

3. The method according to claim 1 wherein the cancer is a solid tumor.

4. The method according to claim 3 wherein the tumor is selected from the group consisting of non-small cell lung carcinoma, prostate carcinoma, renal carcinoma, colon carcinoma, ovarian carcinoma, pancreatic carcinoma and melanoma.

5. The method according to claim 1 wherein $R_1$ and $R_6$ both are $C_1$–$C_6$ alkyl and $R_2$, $R_3$, $R_4$ and $R_5$ are hydrogen.

6. The method according to claim 4, wherein $R_1$ and $R_6$ are ethyl.

7. The method according to claim 6, wherein n, m and p independently are 3 or 4.

8. The method according to claim 6 wherein m, n and p are 3.

9. The method according to claim 3 wherein the anticancer agent is selected from the group consisting of cisplatin, carboplatin, camptothecins, doxorubicin, cyclophosphamide and cloposide.

10. The method according to claim 1, wherein $R_1$ and $R_6$ are both ethyl; $R_2$, $R_3$, $R_4$ and $R_5$ are hydrogen; and n, m and p independently are 3 or 4.

11. The method according to claim 10, wherein m, n, and p are 3.

12. The method according to claim 1 wherein the polyamine is administered intravenously, transdermally, enterally, parenterally, intramuscularly, intranasally, subcutaneously, topically, intravesically, orally or rectally.

13. A method of inducing tumor cell apoptosis in a mammal in need thereof, comprising:

administering to the mammal a therapeutically effective amount of a polyamine of the formula:

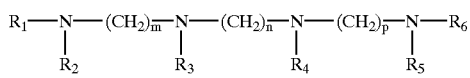

wherein:

$R_1$, $R_2$, $R_3$, $R_4$, $R_5$ and $R_6$ independently are hydrogen or $C_1$–$C_{12}$ alkyl; m, n and p are independently integers from 3 to 6; and at least one of $R_1$, $R_2$, $R_5$, and $R_6$ is $C_1$–$C_{12}$ alkyl; and administering an other anticancer agent therewith.

14. The method of claim 13 wherein the polyamine and anticancer agent are administered as a cocktail.

15. The method of claim 13 wherein the polyamine and anticancer agent are administered in separate unit dosage forms.

16. The method of claim 13 wherein the anticancer agent is selected from the group consisting of cisplatin, carboplatin, camptothecins, doxorubicin, cyclophosphamide and cloposide.

* * * * *

UNITED STATES PATENT AND TRADEMARK OFFICE
CERTIFICATE OF CORRECTION

PATENT NO.    : 6,531,512 B1                                           Page 1 of 1
DATED         : March 11, 2003
INVENTOR(S)   : Kramer et al.

It is certified that error appears in the above-identified patent and that said Letters Patent is hereby corrected as shown below:

Column 1,
Line 8, insert -- This invention was made with Government support under NIHR01CA22153, awarded by the National Institutes of Health. The Government has certain rights in the invention. --

Signed and Sealed this

Twenty-second Day of April, 2003

JAMES E. ROGAN
*Director of the United States Patent and Trademark Office*